United States Patent [19]

Fox

[11] Patent Number: 4,869,415

[45] Date of Patent: Sep. 26, 1989

[54] ENERGY STORAGE MEANS FOR A SURGICAL STAPLER

[75] Inventor: William D. Fox, New Richmond, Ohio

[73] Assignee: Ethicon, Inc., Somerville, N.J.

[21] Appl. No.: 249,537

[22] Filed: Sep. 26, 1988

[51] Int. Cl.[4] .................................................. B25C 5/02
[52] U.S. Cl. ...................................... 227/19; 227/132; 227/146
[58] Field of Search ................... 227/19, 76, 132, 133, 227/146, DIG. 1; 128/334 R

[56] References Cited

U.S. PATENT DOCUMENTS

| 4,184,620 | 1/1980 | Ewig | 227/146 X |
| 4,608,981 | 9/1986 | Rothfuss et al. | 227/19 X |
| 4,633,874 | 1/1987 | Chow et al. | 227/19 X |

Primary Examiner—Donald R. Schran
Assistant Examiner—James L. Wolfe
Attorney, Agent, or Firm—Paul A. Coletti

[57] ABSTRACT

An initiating device which imparts stored potential energy to the driver and cutter in an internal organ stapler. Also disclosed is an overriding device which prevent the use of such a device until the proper clamping of the jaws of the stapler with each other.

13 Claims, 5 Drawing Sheets

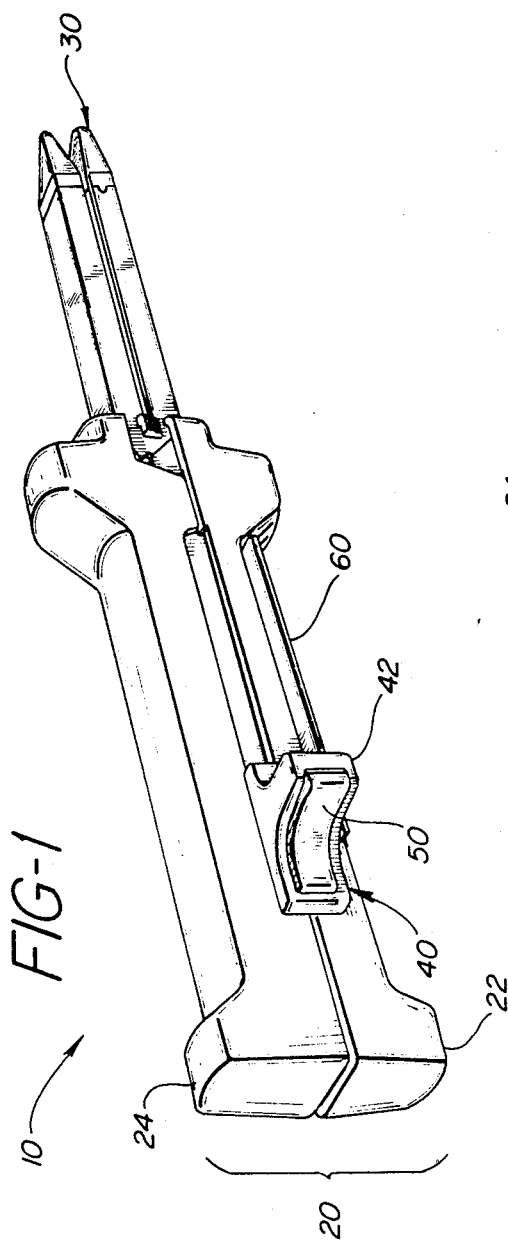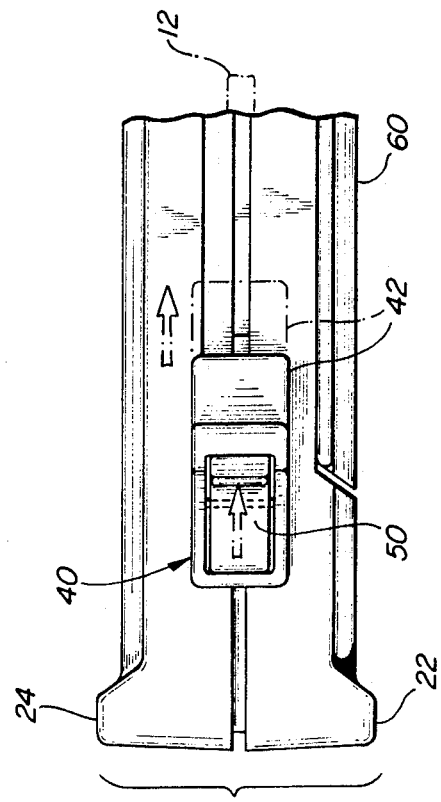

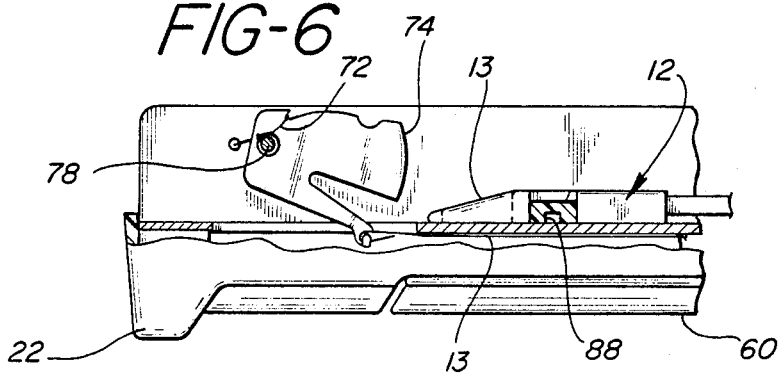
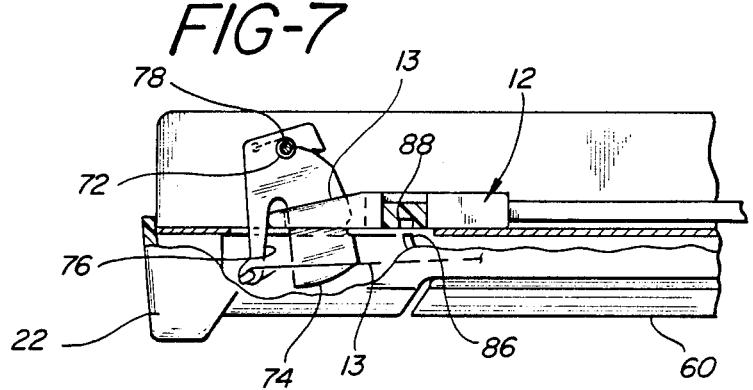
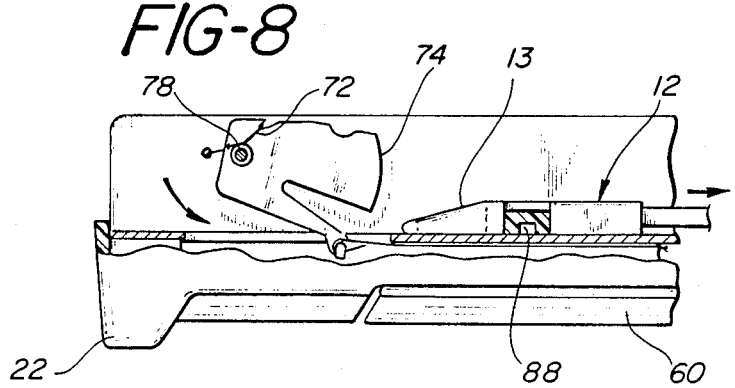

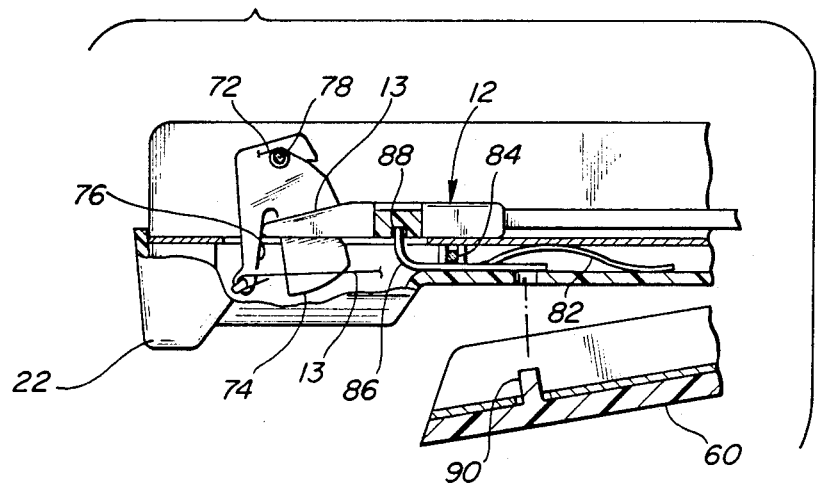

ENERGY STORAGE MEANS FOR A SURGICAL STAPLER

FIELD OF THE INVENTION

This invention relates generally to an improved method for initiating cutting a linear surgical stapler. More specifically, this invention relates to improving initiation of cutting in a surgical stapler by actuating potential energy stored in a spring-activated cammed handle.

BACKGROUND OF THE INVENTION

Recently, surgical staplers have become the more popular mode of use for closing medical wounds. Some of the surgical staplers which have been developed are devices which cut tissue between rows of staples. The tissue is cut while the staples are being driven through the tissue to seal off the wound. This is especially true in gastrointestinal devices.

One of the drawbacks of the presently used surgical stapling and cutting devices is the difficulty of initiating the cutting procedure. That is, generally, the stapler will be comprised of a pair of jaws between which is placed the tissue to be cut and stapled. The jaws are clamped around the tissue, and then the cutting and stapling sequence is initiated. Usually, in order to begin to cut, the user will need to provide extra force at the knife blade. In this regard, the knife blade has encounters difficulty in initially separating the tissue. Once cutting has been initiated, it becomes much easier to cut the remaining tissue. Therefore, only at the moment of beginning cutting is additional force necessary.

SUMMARY OF THE INVENTION

It is, therefore, an object of the present invention to provide a stapler which allows an initial increase in energy at the moment cutting initiates. Therefore, it is an object of the present invention to store potential energy near the actuator of the knife blade.

It is a further object of the present invention to store potential energy near the actuator yet not to permit the use of this potential energy until the stapler is ready for use.

It is yet another object of the present invention to provide a smoother cutting force in a surgical stapler by increasing the force to cut the tissue upon initiation of the stroke for cutting.

These and other objects of the present invention are accomplished in a surgical stapler having stapling and cutting means where energy is stored, and energy storage means which are capable of imparting potential energy to the initiating means of a stapler and cutter. This imparting of potential energy causes said initiating means to overcome resistance imparted by the tissue against the initiating means. In addition, overriding means are provided to prevent the firing of the stapler until the jaws of the surgical stapler are securely clamped one to the other.

DETAILED DESCRIPTION OF THE DRAWINGS

The objects of the present invention will be understood more clearly when taken with the foregoing detailed description of the invention as described with the following drawings, in which:

FIG. 1 is a perspective view of a surgical stapler incorporating the handle which is part of the preferred embodiment of the present invention;

FIG. 2 is an elevational view of the handle of the present invention;

FIGS. 6, 7 and 8 are elevation views of the present invention in the unloaded, loaded, and firing positions, respectively; and FIG. 9 is a cutaway plan view of the overriding mechanism of the preferred embodiment of the present invention.

DETAILED DESCRIPTION OF THE DRAWINGS

Figure 3:
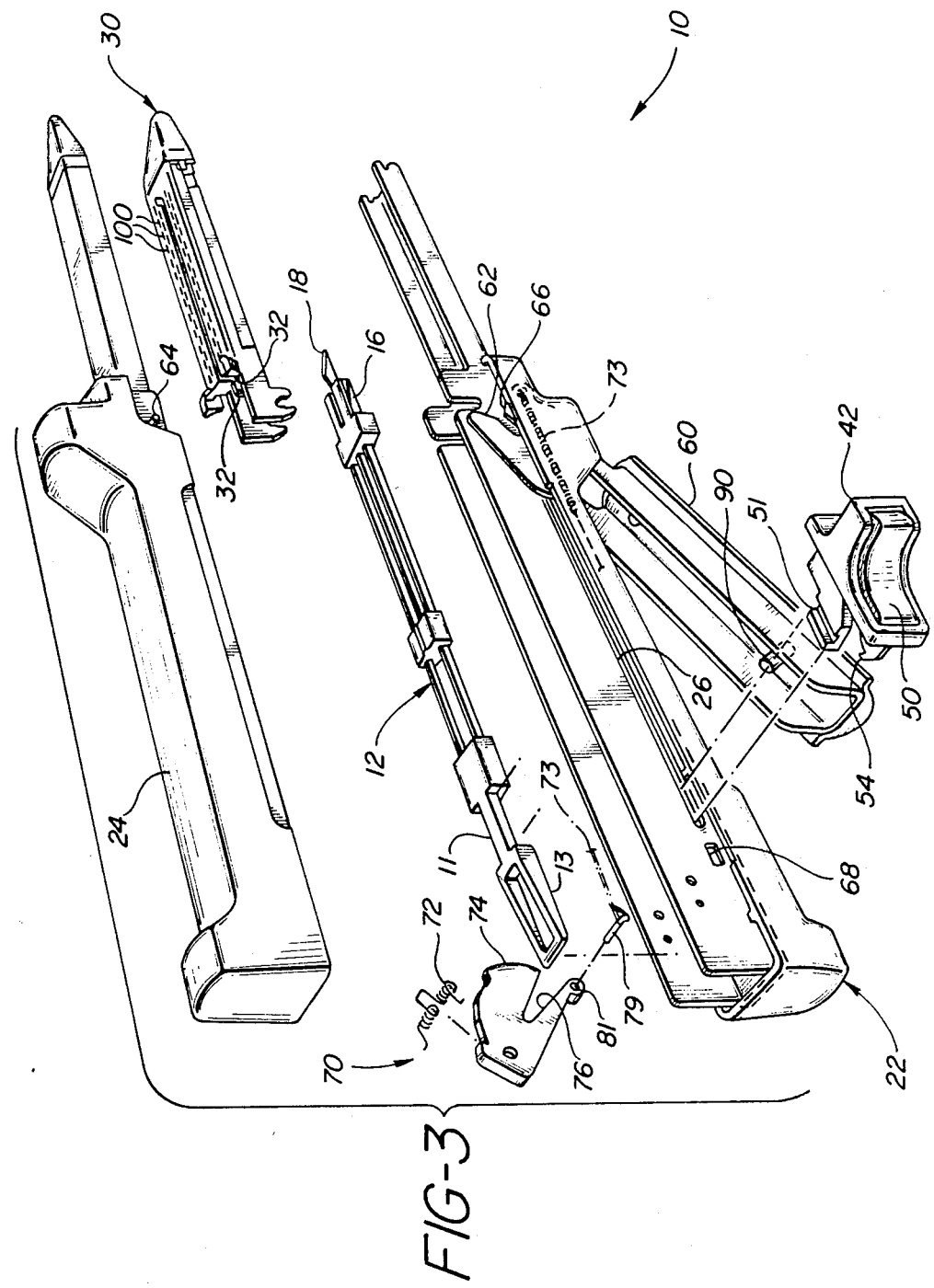
FIG. 3 is an exploded perspective view of a preferred embodiment of the present invention.
Figure 5:
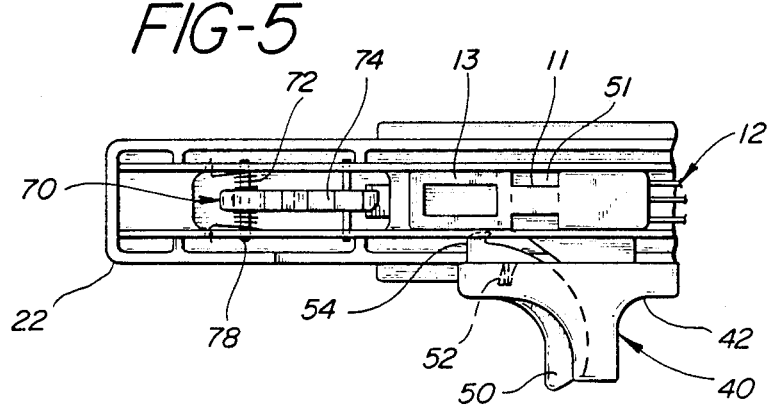

Referring to FIGS. 1, 2, and 3, there is a stapler 10 containing a lower or first jaw 22 and an upper or second jaw 24. These jaws 22, 24 form a stapler body 20. Within the jaws is held tissue, not shown. When a handle 42 is driven along the leg of the stapler 10, it actuates a driving means 12. Guide plate 51 is fitted within mating bar 11 to operate driving means 12. This driving means 12 contains wedges 16 and a knife blade 18. These wedges 16 and knife 18 pass through slots 32 in staple cartridge 30. The wedges 16 activate drivers not shown to cause staples to be driven through staple carriers 100 in the cartridge 30 and onto an anvil at the surface of upper or second jaw 24, While the stapler 10 is driving staples, one stroke of the handle 42, there are formed two rows of staples within the tissue, which has been cut between these two rows. The improvement to the present stapler 10 is most basically seen in the conversion of handle 42 to initiating means 40. In the initiating means 40 there is a first detent means 50 incorporated on the handle 42. This will be best seen in FIG. 5. The first detent means 50 pivots around pivot 52 along handle 42. The detent means 50 contains a dowel or post 54 which is able to be placed within slot 68 on the lower or first jaw 22 of the stapler 10, as seen in FIG. 3.

Figure 4:
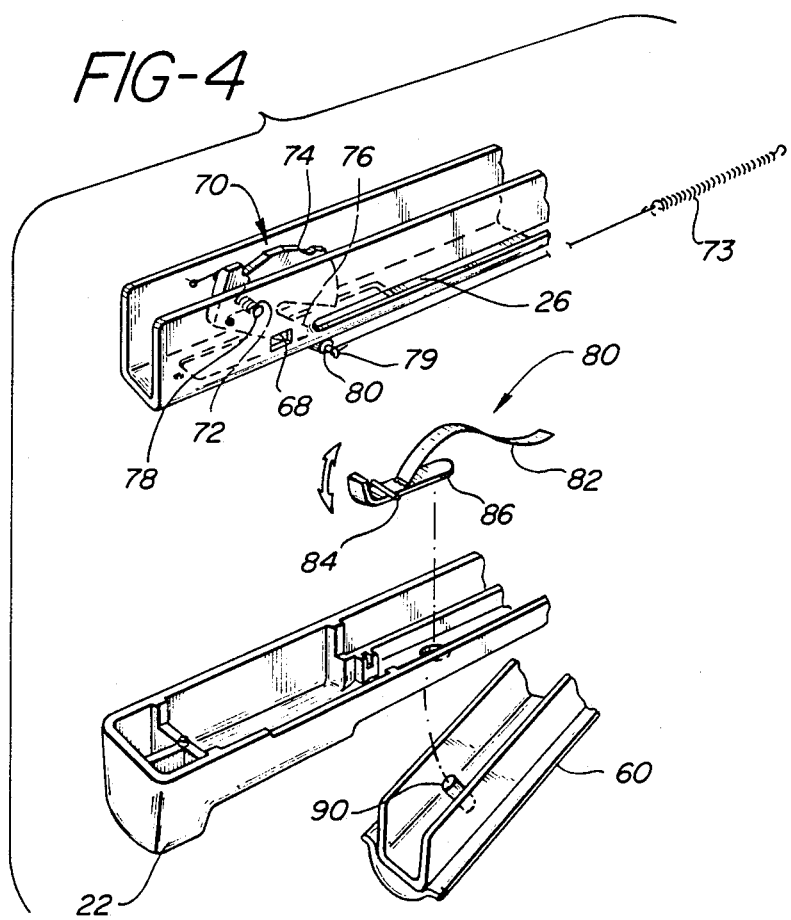
FIG. 4 is an exploded perspective view of the lower jaw mechanism employing a preferred embodiment of the present invention.

In addition, in one preferred embodiment there is also seen in FIG. 4 spring 73, attached along the lower jaw 22 at one end. Spring 73 is also attached to energy storage means 70, at attachment post 79, which is fit within hole 81 on energy storage means 70. This energy storage means 70 is also spring loaded, by means of spring 72, to the lower jaw 22 within guiding chamber 26. The springs 72, 73 will store potential energy when the initiating means 40 is in its loaded position.

Energy storage means 70 also contains cam 74 with groove 78, as best seen in FIGS. 4 through 9. It will be energy means 70 which will enable the initiating means 40 to supply additional energy to the cutter 18 and the wedges 16 during initiating of the cutting and stapling stroke.

Also seen in FIG. 4, as well as in FIG. 9, is overriding or second detent means 80. This overriding means 80 comprises spring 82 which is loaded against the guiding chamber 26. There is also seen a hooking bar 86, which rotates around pivot 84. This hooking bar 86 has a curved end which fits within mating groove 88 of driving means 12, as best seen in FIGS. 6 and 7. The overriding means can be activated by peg 90 placed within lever 60 of the lower jaw 22. It will be this peg 90 which enables overriding means 80 to be deactivated for actuation of means 70 to provide potential energy to initiating means 40 at the start of the stroke.

Therefore, the present invention will be practiced as follows. First, tissue will be placed between the two jaws 22, 24. Then lever 60 will be clamped using clamp 62 around pin 64 in tandem with mating notch 66. At that point, the dowel 54 of first detent means 50 has previously been inserted into slot 68 on guiding chamber 26 of lower jaw 22. First detent means 50 is then pivoted about pivot 52 to release dowel 54 from slot 68. Once the tissue is held, initiating means 40 is moved forward (toward the end of jaws 22, 24) causing driving means 12 to activate energy storage means 70. Energy storage means 70 is then rotated when pusher block 13 contacts groove 76 to turn cam 74. Springs 72, 73 then are ready to release their stored potential energy. The stapler 10 is then ready for cutting and stapling use.

The stapler can only be used if peg 90 of lever 60 has deactivated overriding means 80. This will occur when the peg 90 has been rotated its maximum distance, upon the proper clamping of lever 60. One should note that hooking bar 86 of overriding means 80 will have been placed within the mating groove 88 located on driving means 12. It will only be if peg 90 pivots overriding means 80 around pivot 84 that the hooking bar 86 will be displaced outside mating groove 88. Only then will second detent means 80 be deactivated. Only then will the stapler 10 allow use of first detent means 50.

At this point, first detent means 50 can be pivoted around pivot 52 to allow use of handle 42. The energy stored in springs 72, 73 then cause cam 74 to impart the stored potential energy on pusher block 13 of driving means 12. This stored potential energy allows for an initiating energy to be imparted on the cutter 18 and the stapling wedges 16. This stored potential energy initiates the cutting and stapling stroke more easily, allowing for better, easier and more accurate stapling and cutting.

Therefore, the present invention can be used in all staplers which need additional initiating energy, particularly staplers which use cutting devices. Also, while this particular invention has been described in connection with the presently preferred embodiment, it will be understood that its scope is to include any modifications to the invention which cause substantially similar functions to be performed substantially the same way. Furthermore, it is recognized that the invention is described in connection with the attached claims and their equivalents in which:

What is claimed is:

1. In a surgical stapler having initiating means capable of activating driving means for driving staples into tissue, the improvement comprising energy storage means capable of imparting potential energy to said initiating means, said imparted energy causing said initiating means to overcome forces imparted by said tissue against said initiation means, said energy storage means comprising spring means connected to a camming means having a groove and the body of said stapler, said spring means capable of having potential energy imparted thereon by the user, said potential energy held in place on said camming means by first detent means attached to said stapler body and capable of holding said initiating means in place on said stapler until ready for use, said initiating means capable of displacing said detent means and said potential energy on said initiating means during use.

2. In the surgical stapler of claim 1, said initiating means comprising handle means connected to said driving means, said handle means terminating in a dowel insertable in said camming means of said energy storage means, and held within said groove until the disengaging of said first detent means.

3. In the surgical stapler of claim 2, said first detent means pivotable on said handle means and culminating in a peg insertable in a slot on said stapler body in order to hold said handle means and said energy storage means stable until said stapler is ready for use, upon which said first detent means is pivoted out of said slot and said potential energy is imparted on said handle means.

4. In the surgical stapler of claim 3, wherein said stapler comprises a first jaw attachable to a second jaw to fit around said tissue, the improvement further comprising overriding means capable of holding said energy storage means and said cutting means in place until said jaws are properly attached to each other.

5. In the surgical stapler of claim 4, wherein said first jaws is attached to said second jaw by means of a clamp actuating a lever on said first jaw, said overriding means comprising second detent means spring-loaded and insertable into said driving means, said second detent means pivotable out of said driving means by contact with a peg located on said lever upon the closing of said first and second jaws.

6. In the surgical stapler of claim 5, said second detent means comprising a hooking bar capable of being hooked onto a mating groove located on said driving means in order to hold said drawing means in place until said second detent means is pivoted out of said driving means.

7. In the surgical stapler of claim 1 wherein said stapler comprises a first jaw attachable to a second jaw to fit around said tissue, the improvement further comprising overriding means capable of holding said energy storage means in place until said jaws are properly attached to each other.

8. In the surgical stapler of claim 7 wherein said first jaw is attached to said second jaw by means of a clamp actuating a lever on said first jaw, said overriding means comprising second detent means spring-loaded and insertable into said driving means, said second detent means pivotable out of said driving means by contact with a peg located on said lever upon closing of said first and second jaws.

9. In the surgical stapler of claim 8, said second detent means comprising a hooking bar capable of being hooked onto a mating groove located on said driving means.

10. A surgical stapler comprising:
a first jaw attachable to a second jaw by means of a clamp activated by a lever on said first jaw;
driving means for driving staples located on one of said jaws into tissue placed between said jaws;
a handle connected to said driving means for guiding said driving means within said stapler;
said driving means insertable in camming means attached to one of said jaws by a loadable spring;
said handle having a dowel insertable on a slot within one of said jaws to hold said handle and said loaded spring in place until said stapler is ready for use, whereupon said dowel is pivoted out of said slot and potential energy from said spring is imparted by said camming means on said driving means to overcome forces imparted by said tissue against said driving means and said handle.

11. The surgical staple of claim 10 wherein said first jaw further comprises a peg located on said lever and a hooking bar spring-loaded and pivotable into a mating groove on said driving means, said hooking bar holding said driving means within said stapler, until said peg pivots said hooking bar out of said mating groove upon the proper clamping of said first jaw to said second jaw of said stapler.

12. The surgical stapler of claim 11 wherein the pivoting of said hooking bar permits said handle to be pivoted out of said slot and the imparting of said potential energy by said camming means spring on said driving means and handle.

13. A method for overcoming forces by tissue against staples in a surgical stapler having driving means and means for initiating said driving means comprising:

storing potential energy in said initiating means until said stapler is ready for stapling, then imparting said potential energy on said driving means through said initiating means.

* * * * *